United States Patent [19]

Caufield et al.

[11] Patent Number: 5,525,610
[45] Date of Patent: Jun. 11, 1996

[54] 42-EPI-RAPAMYCIN AND PHARMACEUTICAL COMPOSITIONS THEREOF

[75] Inventors: Craig E. Caufield; Alexander A. Grinfeld, both of Princeton Junction, N.J.

[73] Assignee: American Home Products Corporation, Madison, N.J.

[21] Appl. No.: 429,374

[22] Filed: Apr. 26, 1995

Related U.S. Application Data

[63] Continuation-in-part of Ser. No. 221,716, Mar. 31, 1994, abandoned.

[51] Int. Cl.$^6$ ............ A61K 31/55; C07D 496/04; C07D 496/14; C07D 491/04; C07D 491/14
[52] U.S. Cl. ............................. 514/291; 540/456
[58] Field of Search ..................... 540/456; 514/291

[56] References Cited

U.S. PATENT DOCUMENTS

| | | | |
|---|---|---|---|
| 3,929,992 | 12/1975 | Sehgal et al. | 514/291 |
| 3,993,749 | 11/1976 | Sehgal et al. | 514/291 |
| 4,316,885 | 2/1982 | Rakhit | 514/291 |
| 4,375,464 | 3/1983 | Sehgal et al. | 514/291 |
| 4,401,653 | 8/1983 | Eng | 514/291 |
| 4,650,803 | 3/1987 | Stella et al. | 514/291 |
| 4,885,171 | 12/1989 | Surendra et al. | 514/291 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 514/291 |
| 5,080,899 | 1/1992 | Sturm et al. | 514/291 |
| 5,091,389 | 2/1992 | Ondeyka et al. | 514/291 |
| 5,100,883 | 3/1992 | Schiehser | 514/291 |
| 5,100,899 | 3/1992 | Calne | 514/291 |
| 5,102,876 | 4/1992 | Caufield | 514/291 |
| 5,118,677 | 6/1992 | Caufield | 514/291 |
| 5,118,678 | 6/1992 | Kao et al. | 514/291 |
| 5,120,726 | 6/1992 | Failli et al. | 514/291 |
| 5,120,842 | 6/1992 | Failli et al. | 514/291 |
| 5,130,307 | 7/1992 | Failli et al. | 514/291 |
| 5,138,051 | 8/1992 | Hughes et al. | 514/291 |
| 5,151,413 | 9/1992 | Caufield et al. | 514/291 |
| 5,169,851 | 12/1992 | Hughes et al. | 514/291 |
| 5,177,203 | 1/1993 | Failli et al. | 514/291 |
| 5,194,447 | 3/1993 | Kao | 514/291 |
| 5,221,670 | 6/1993 | Caufield | 514/291 |
| 5,233,036 | 8/1993 | Hughes | 514/291 |
| 5,258,389 | 11/1993 | Goulet et al. | 514/291 |
| 5,260,300 | 11/1993 | Hu | 514/291 |
| 5,262,423 | 11/1993 | Kao | 514/291 |
| 5,286,730 | 2/1994 | Caufield et al. | 514/291 |
| 5,286,731 | 2/1994 | Caufield et al. | 514/291 |
| 5,288,711 | 2/1994 | Mitchell et al. | 514/291 |

FOREIGN PATENT DOCUMENTS

| | | | |
|---|---|---|---|
| 507555A1 | 7/1992 | European Pat. Off. | 514/291 |
| 9402136 | 2/1994 | WIPO | 514/291 |
| 9402485 | 2/1994 | WIPO | 514/291 |
| 9402137 | 2/1994 | WIPO | 514/291 |

OTHER PUBLICATIONS

Kao et al., Commonly owned U.S. patent application Ser. No. 08/054,655 Filed: Apr. 23, 1993.
Venzina, C., J. Antibiot. 28:721 (1975).
Sehgal, S. N., J. Antibiot 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

Primary Examiner—Robert T. Bond
Attorney, Agent, or Firm—Steven R. Eck

[57] ABSTRACT

This invention comprises the compound of 42-Epimer Rapamycin of the following structural formula:

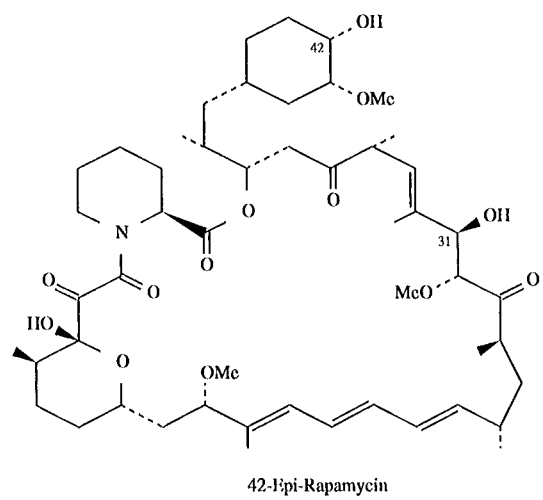

42-Epi-Rapamycin as well as pharmaceutical compositions containing 42-Epi-Rapamycin and its use in methods for inducing immunosuppression and methods for treating transplantation rejection, graft vs. host disease, autoimmune diseases, diseases of inflammation, solid tumors, fungal infections, adult T-cell leukemia/lymphomas and hyperproliferative vascular disorders.

7 Claims, No Drawings

42-EPI-RAPAMYCIN AND PHARMACEUTICAL COMPOSITIONS THEREOF

RELATED APPLICATIONS

This is a continuation-in-part of U.S. Ser. No. 08/221,716, filed Mar. 31, 1994, now abandoned.

This invention relates to an epimer of rapamycin, specifically 42-epi-rapamycin or pharmaceutically acceptable salts thereof, and pharmaceutically useful compositions containing 42-epi-rapamycin, or its pharmaceutically acceptable salts, which are useful in medically-related administrations for inducing immunosuppression and for treating transplantation rejection, graft vs. host disease, autoimmune diseases, diseases of inflammation, solid tumors, fungal infections, adult T-cell leukemia/lymphomas and hyperproliferative vascular disorders.

BACKGROUND OF THE INVENTION

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

U.S. Pat. No. 5,100,899 (Calne) discloses methods of inhibiting transplant rejection in mammals using rapamycin and derivatives and prodrugs thereof. Other chemotherapeutic agents listed for use with rapamycin are azathioprine, corticosteroids, cyclosporen (and cyclosporin A), and FK-506, or any combination thereof.

DESCRIPTION OF THE INVENTION

The present invention provides an epimer of rapamycin, and the pharmaceutically acceptable salts thereof, which is useful as an antifungal agent and useful in medically-related administrations for inducing immunosuppression and for treating transplantation rejection, graft vs. host disease, autoimmune diseases, diseases of inflammation, solid tumors, fungal infections, adult T-cell leukemia/lymphomas and hyperproliferative vascular disorders. The compounds of the present invention possess the general structure of rapamycin, with an epimeric difference in the configuration of the 42-position hydroxyl group, as illustrated by the structures below:

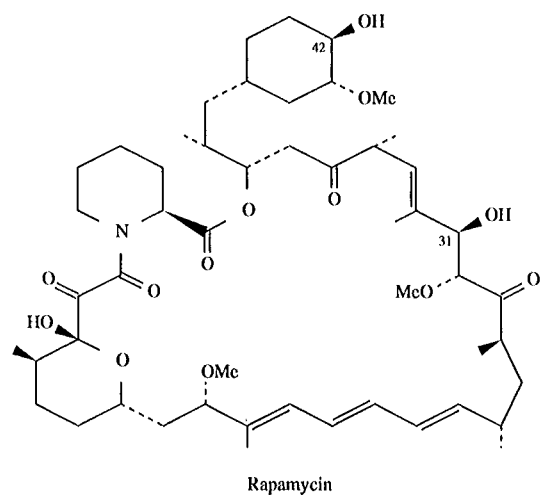

Rapamycin

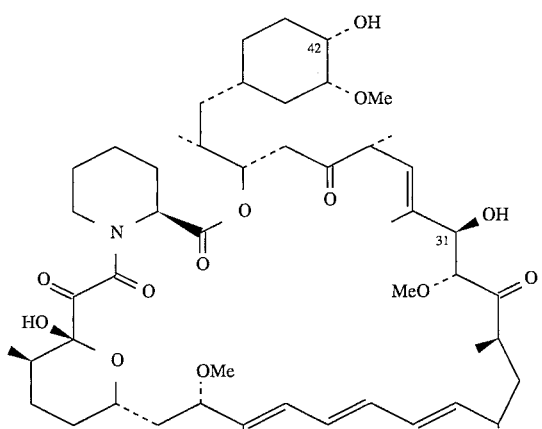

42-Epi-Rapamycin

The compound of this invention, 42-Epi-Rapamycin, can be produced by the reduction of 42-oxorapamycin with a solution of KPh$_3$BH in THF at a temperature of about −78° C. for about 2 hours, as depicted below:

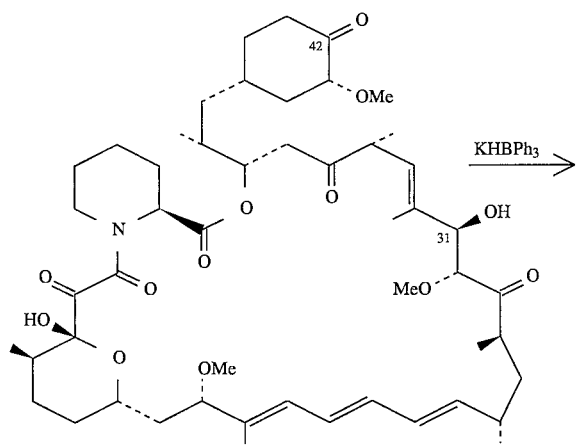

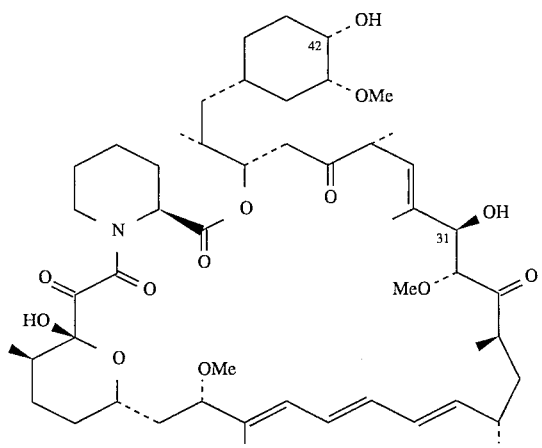

With the use of KHBPh$_3$ as a reducing agent, substantially all of the 42-oxorapamycin is reduced to the desired 42-Epi-Rapamycin. Conducting the reaction with other preferred reducing agents, such as LiAl(O-t-Bu)$_3$H, NaBH$_4$, and L-Selectride, under similar conditions provides varying amounts of 42-Epi-Rapamycin and Rapamycin, as depicted by the reaction scheme and Table 1 below:

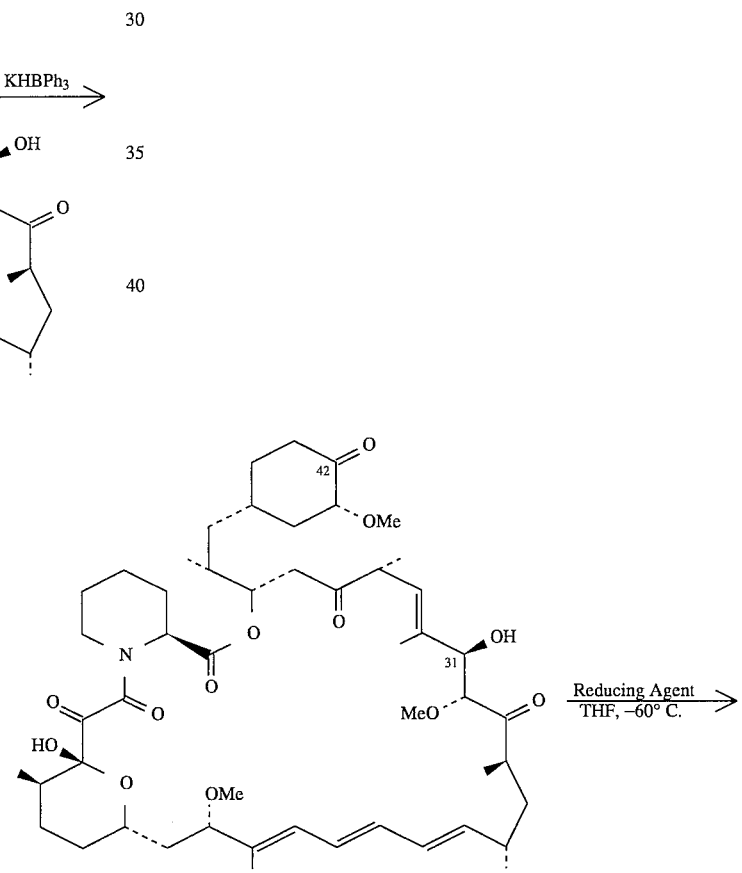

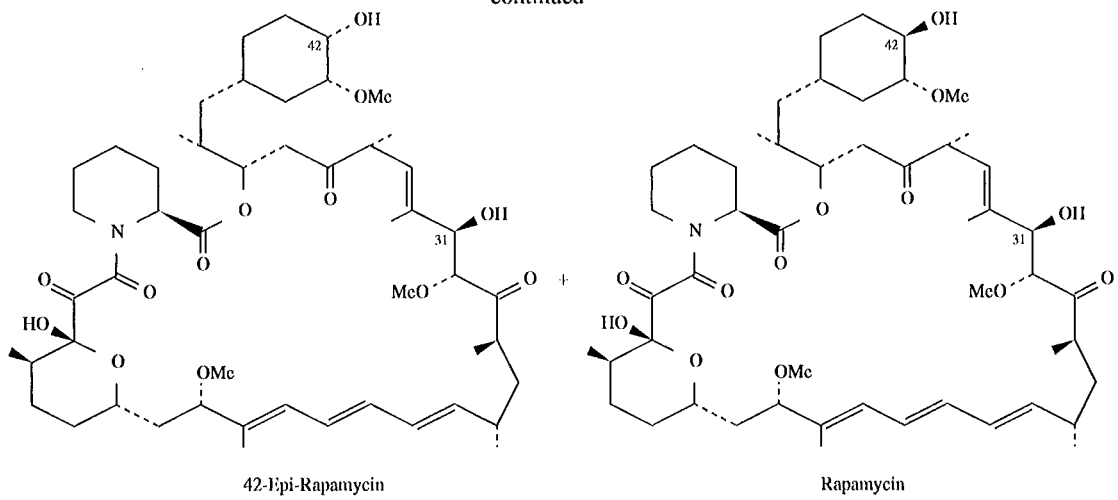

42-Epi-Rapamycin          Rapamycin

TABLE 1

| Reducing Agent | % 42-Epi-Rapamycin | % Rapamycin |
|---|---|---|
| KBPh$_3$H | 100 | 0 |
| LiAl(O-t-Bu)$_3$H | 50 | 50 |
| NaBH$_4$ | 40 | 60 |
| L-Selectride | 100 | 0 |
| NaBH$_3$CN | no reaction | |

Alternatively, 42-Epi-Rapamycin can be synthesized from Rapamycin, itself, by treating the Rapamycin with one equivalent of trifluoromethanesulfonic anhydride in the presence of a suitable base, such as 2,6-di-tert-butyl-4-methylpyridine, followed by the addition of a solution of dimethylsulfoxide/water, as depicted below:

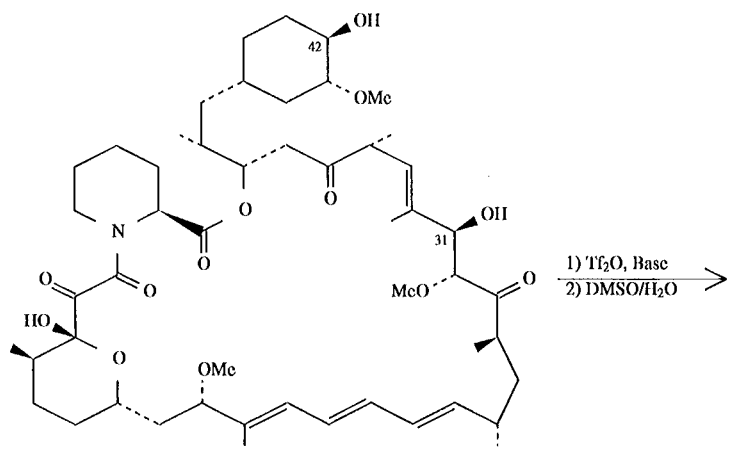

-continued

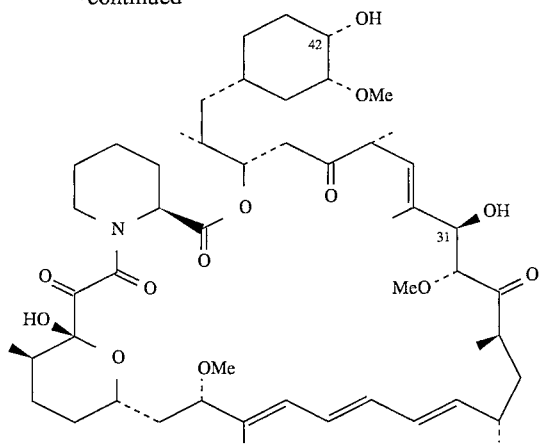

42-Keto-Rapamycin can be reduced to 42-Epi-Rapamycin by treatment with excess diisobutylaluminum hydride (i-Bu$_2$AlH or DIBAL-H) at a temperature of about −60° C. As the scheme below indicates, treatment of 42-Keto-Rapamycin with about 4 equivalents of i-Bu$_2$AlH reduces 42-Keto-Rapamycin's 15 position and a subsequent addition of about 4 equivalents of i-Bu$_2$AlH leads to a reduction at the 42 position, yielding 42-Epi-Rapamycin.

Alternatively, 42-Epi-Rapamycin can be formulated from Rapamycin through Rapamycin 42-trifluoromethane sulfonate. This can be accomplished by treating Rapamycin in a reaction medium containing an acylating agent, such as triflic anhydride or triflic chloride, and a base, such as pyridine, picolines, lutidines, or 2,6-ditertbutylpyridine, in an inert organic solvent, such as CH$_2$Cl$_2$, CH$_2$ClCH$_2$Cl or CCl$_4$.

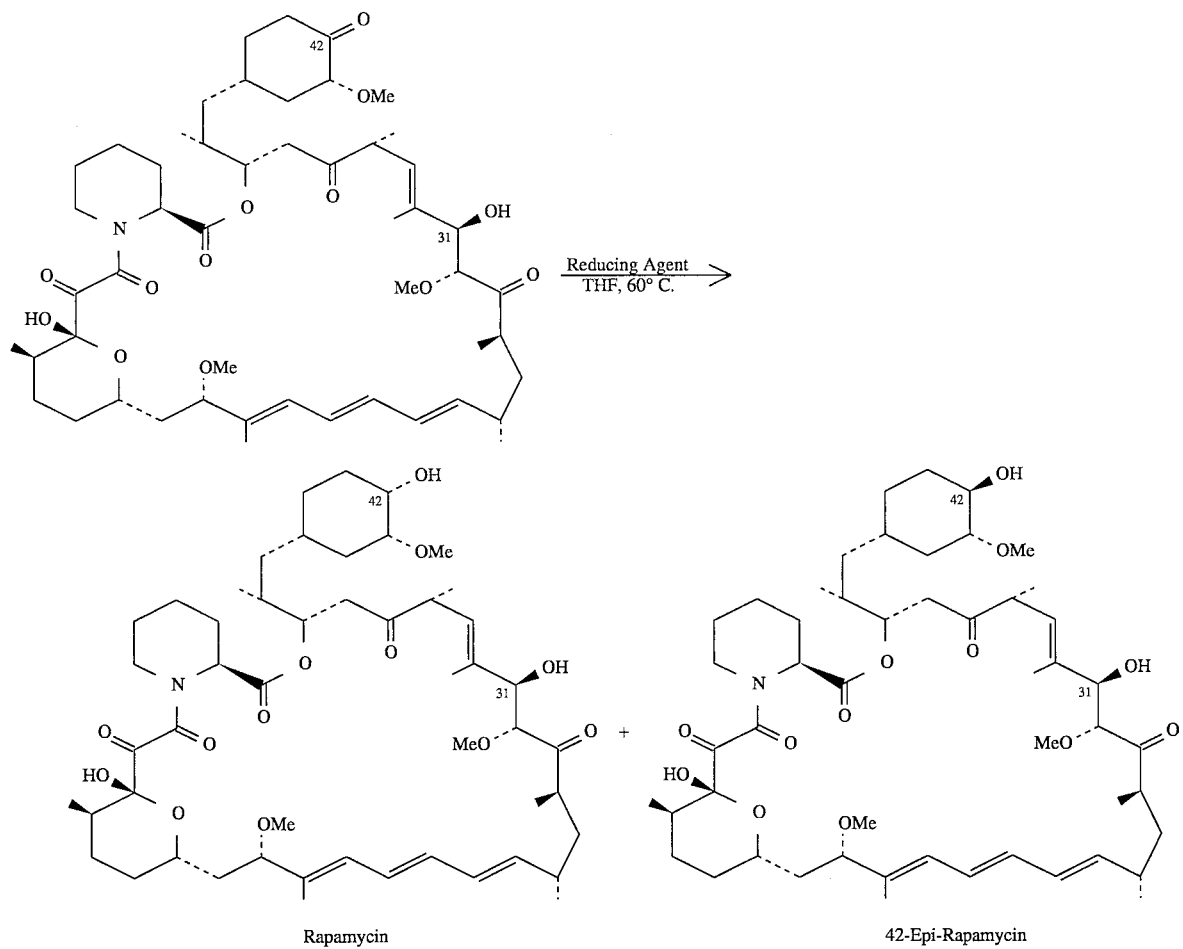

The pharmaceutically acceptable salts of the present compounds are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

These compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, gidants, compression aids, binders or table-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredients can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably a sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The dosage requirements will vary with the particular pharmaceutical composition employed, the route of administration, the severity of the symptoms presented and the particular subject being treated. Based on the results obtained in the standard pharmocological test procedures, projected daily dosages of active compound would be from about 0.1 µg/kg to about 100 mg/kg, preferably between 0.001–25 mg/kg, and more preferably between 0.01–5 mg/kg. Treatement will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based upon experience with the individual subject treated. Preferably, the pharmaceutical composition is in unit dosage form, e.g. as tablets or capsules. In such form, the composition is subdivided in unit dose(s) containing appropriate quantities of the active ingredient; the unit dosage forms can be packaged compositions, for example, packeted powders, vials, ampoules, prefilled syringes or sachets containing liquids. the unit dosage form can be, for example, a capsule or tablet itself, or it can be the appropriate number of any such compositions in package form.

In addition, the compounds of this invention may be employed as a solution, cream, or lotion by formulation with pharmaceutically acceptable vehicles containing 0.5–5 percent, preferably about 2%, of active compound which may be administered to a fungally affected area.

Immunosuppressive activity for representative compounds of this invention was evaluated in an in vitro standard pharmacological test procedure to measure lymphocyte proliferation (LAF) and in one in vivo standard pharmacological test procedure. The pinch skin graft test procedure measures the immunosuppressive activity of the compound tested as well as the ability of the compound tested to inhibit or treat transplant rejection. The procedures for these standard pharmacological test procedures are provided below at the end of Example 1.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 3.8 to 4.1. The results obtained are provided as an $IC_{50}$.

42-epimer rapamycin was also evaluated in an in vivo test procedure designed to determine the survival time of pinch skin graft from male BALB/c donors transplanted to male $C_3H(H-2K)$ recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of the test compound intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg.

The results obtained in these standard pharmacological test procedures are provided at the end of Example 1, below.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft test procedure. Additionally, the results obtained in the skin graft standard pharmacological test procedure further demonstrate the ability of 42-Epi-Rapamycin to treat or inhibit transplantation rejection and graft vs. host disease.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis.

When administered for the treatment or inhibition of the above disease states, 42-Epi-Rapamycin can be administered to a mammal in any manner that provides the desired therapeutic levels of 42-Epi-Rapamycin. These methods of administration include oral, parenteral, intranasal, intrabronchial, transdermal, topical, intravaginal, or rectal administrations.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The following examples illustrate the production of the Rapamycin 42-epimers of the present invention.

EXAMPLE 1

42-Epi-Rapamycin ($C_{51}H_{79}NO_{13}$, MW=914)

To a solution of 10 g (11 mmol) of Rapamycin in 200 ml of acetonitrile was added 3.8 g (3 equivalents) of N-methyl morpholine N-oxide and then 193 mg (0.55 mmol, 0.95 equivalents) of tetra-n-propylammonium perruthenate. Additional perruthenate (193 mg) was added after 15 minutes and after 2 hours. One hour after the last addition, the acetonitrile was removed in vacuo and the residue was filtered through 60–200 mesh silica gel using ethyl acetate as an eluting solvent. Flash chromatography on 60–200 mesh silica gel using haxane/ethyl acetate as the eluant gave, after trituration with ethyl ether, 740 mg of 42-oxorapamycin and 820 mg of rapamycin.

Residual fractions containing primarily rapamycin and 42-oxorapamycin were combined and reoxidized two times (sequentially) to give crude title compound. Gravity chromatography on 60–200 mesh silica gel using ethyl acetate as the eluant gave an additional 1.0 g of 42-oxorapamycin after removal of solvent from the appropriate fractions and trituration with ethyl ether.

Anal. Calcd.: C, 67.15; H, 8.51; N, 1.54 Found: C, 66.90; H, 8.32; N, 1.65

To a solution of 42-oxorapamycin (914 mg, 1 mmol) in 50 ml of dry THF cooled to −78° C. was added portionwise over 30 minutes a solution of $KBPh_3H$ (2 mL of 0.5M solution, 1 mmol) in THF. The mixture was stirred for 2 hours at −78° C. TLC analysis (100% EtOAc) indicated the absence of starting material in the reaction mixture. The cooling bath was removed and the mixture was quenched with 50 mL of water and 50 ml of brine. The product was extracted with EtOAc (3×5 ml). The combined organic layers were washed with saturated sodium bicarbonate solution and dried over sodium sulfate. The residue, after removal of the solvent, was subjected to flash chromatography eluting under gradient conditions (50% EtOAc:Hexane to 65% EtOAc:Hexane). Removal of solvent from fractions containing 42-epirapamycin afforded 630 mg (70%) of pure product. Spectral data follows. $^1$H NMR (300 MHz, $CDCl_3$) δ5.9–6.5 (m, 4H, vinylic), 5.5 (m, 1H, vinylic), 4.2 (d, 1H), 4.1 (m, 1H), 3.38 (s, 3H, $CH_3O$—), 3.34 (s, 3H, $CH_3O$—), 3.14 (s, 3H, $CH_3O$—); MS (neg-.FAB): 913 [M]$^-$, 590.3, 167.1.

LAF IC$_{50}$: 5.00 and 7.50 nM

Skin Graft Survival Time: 10.2±1.3 and 10.8±0.5 days

EXAMPLE 2

Alternative Procedure for the Synthesis of 42-Epi-Rapamycin

To a solution of 0.914 g (1 mmol) of rapamycin and 615 mg (3 mmol) of 2,6-di-tert-butyl- 4-methylpyridine in 15 ml of dichoromethane at 0° C. was added dropwise over 5 minutes, 310 mg( 187 μL, 1.1 mmol) trifluoromethanesulfonic anhydride. The solution was kept at 0° C. for 30 minutes when the ice bath was removed. The solution was stirred at room temperature for 30 minutes when 180 μL (10 mmol) of water and 1.5 ml (10% volume) of DMSO was added. The mixture was stirred at room temperature for 24 h when TLC (silica, ethyl acetate) showed disappearance of the 42-Rapamycin triflate. The reaction mixture was quenched with water, extracted three times with ethyl acetate, combined organics were washed with 0.5N HCl, saturated $NaHCO_3$, and brine. The solution was dried over anhydrous sodium sulfate, filtered, and concentrated in vacuo to afford a pale yellow product. The product was purified by preparative HPLC (2" Dynamax silica column, 60% ethyl acetate/hexane, 20 ml/min) to give 530 mg (58%) of compound. Analysis of this compound indicated that it was identical to that obtained from the procedure of Example 1, above.

EXAMPLE 3

The position-42 epimer of rapamycin was evaluated in an in vivo test procedure designed to determine the survival time of pinch skin graft from male BAB/c donors trnasplanted to male C₃H(H-2K) recipients. This method is adapated from Billingham, R. E. and Medawar, P. B., J. Exp. Biol. 28:385–402, (1951). Briefly, a pinch skin graft from the donor was grafted on the dorsum of the recipient as an allograft, and an isograft was used as a control in the same region. The recipients were treated with the test compounds intraperitoneally or orally. Rapamycin was used as a test control and untreated recipients were used as a rejection control. The graft was monitored daily and observations were recorded until the graft became dry and formed a blackened scab. This was considered as the grafts rejection day. The mean graft survival time (number of days±S.D.) of the drug treatment group was compared with the control group. Untreated (control) pinch skin grafts are usually rejected within 6–7 days.

As indicated in Example 1, 42-Epi-Rapamycin was tested in the pinch skin graft test at a dose of 4 mg/kg and was found to produce survival times of 10.2±1.3 days and 10.8±0.5 days. These survival times resulting from treatment with 42-Epi-Rapamycin can be compared to those provided below for Rapamycin and its analogs 31-Oxorapamycin, 1,2-Dihydrorapamycin, and 1,2,3,4-Tetrahydrorapamycin:

2. A method of inducing immunosuppression in a mammal in need thereof, which comprises administering an immunosuppressive effective amount of a compound of the structure:

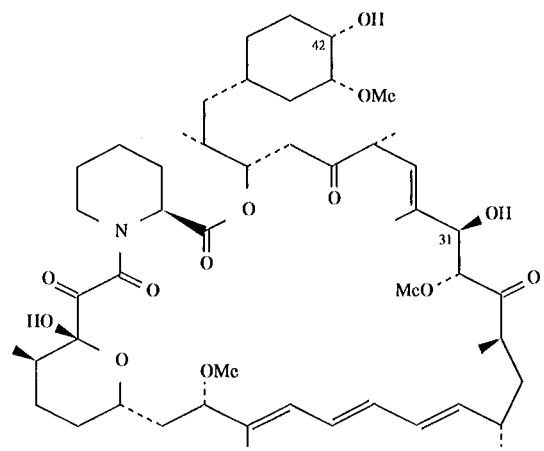

or a pharmaceutically acceptable salt thereof.

3. A method of treating transplantation rejection or host vs. graft disease in a mammal in need thereof which comprises administering an antirejection effective amount of a compound of the structure:

| Compound | $R^1$ | $R^2$ | $R^3$ | $R^4$ | $R^5$ | $R^6$ | other | TP Test (ratio) | Skin Graft (days) |
|---|---|---|---|---|---|---|---|---|---|
| Rapamycin | —OH | OH | =O | OMe | OMe | =O | | 1 | 11.66 ± 0.47 |
| 31-Oxorapamycin | —OH | =O | =O | OMe | OMe | =O | | 0.002 | 8.7 ± 0.8 |
| 1,2-Dihydro-rapamycin | OH | OH | =O | OMe | OMe | =O | 1,2-bonds reduced | 0.12 | 7.3 ± 0.9 |
| 1, 2, 3, 4-Tetrahydro-rapamycin | —OH | OH | =O | OMe | OMe | =O | 1, 2, 3, 4-bonds reduced | 0.04 | 7.0 ± 0.9 |

What is claimed:

1. A compound of the structure:

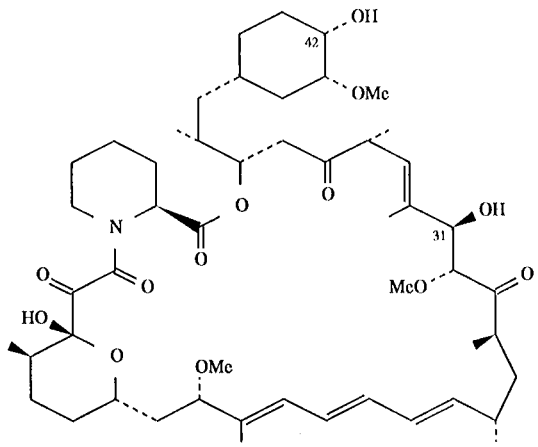

or a pharmaceutically acceptable salt thereof.

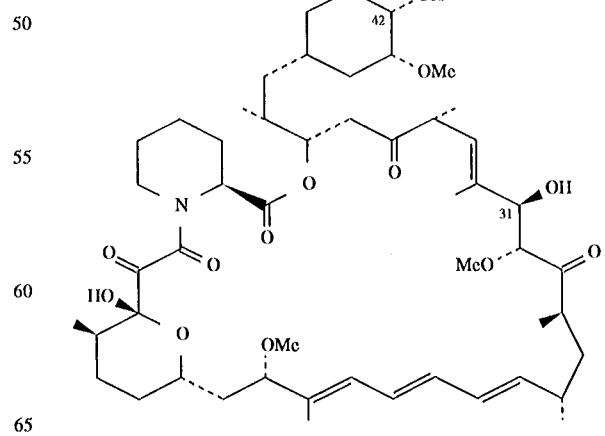

or a pharmaceutically acceptable salt thereof.

4. A method of treating rheumatoid arthritis in mammal in need thereof which comprises administering an antiarthritis effective amount of a compound of the structure:

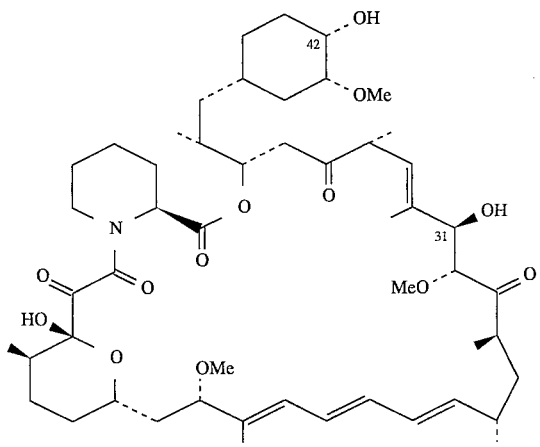

or a pharmaceutically acceptable salt thereof.

5. A pharmaceutical composition which comprises an amount of a compound of the structure:

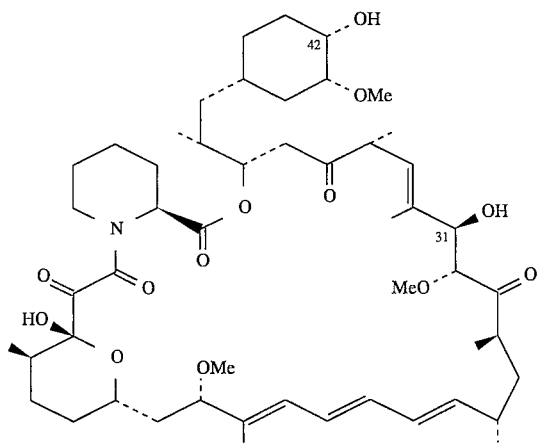

or a pharmaceutically acceptable salt thereof which is effective to induce immunosuppression in a mammal along with a suitable pharmaceutical carrier.

6. A pharmaceutical composition which comprises an amount of a compound of the structure:

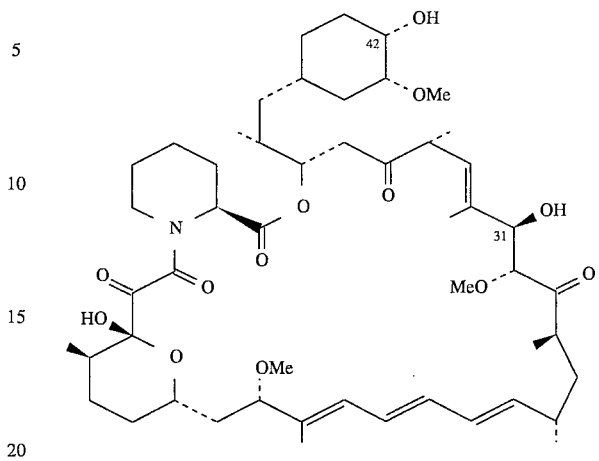

or a pharmaceutically acceptable salt thereof which is effective to treat transplantation rejection or host vs. graft disease in a mammal along with a suitable pharmaceutical carrier.

7. A pharmaceutical composition which comprises an amount of a compound of the structure:

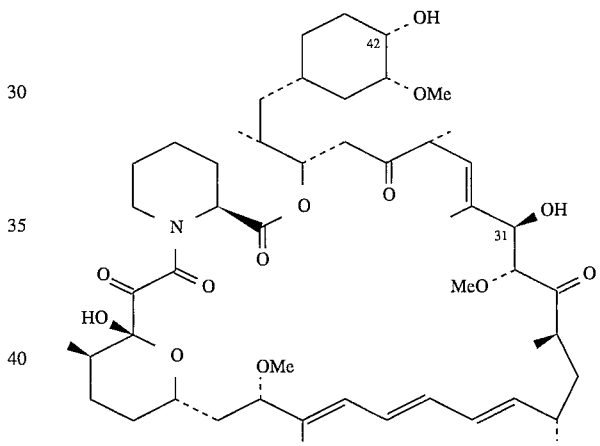

or a pharmaceutically acceptable salt thereof which is effective to treat rheumatoid arthritis in a mammal along with a suitable pharmaceutical carrier.

* * * * *